US00PP22541P3

(12) United States Plant Patent
Vorsa

(10) Patent No.: US PP22,541 P3
(45) Date of Patent: Mar. 6, 2012

(54) CRANBERRY PLANT NAMED 'CNJ95-20-20'

(50) Latin Name: ***Vaccinium macrocarpon* Ait.**
Varietal Denomination: CNJ95-20-20

(75) Inventor: Nicholi Vorsa, Atco, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 12/802,279

(22) Filed: Jun. 2, 2010

(65) Prior Publication Data

US 2011/0302678 P1 Dec. 8, 2011

(51) Int. Cl.
*A01H 5/00* (2006.01)

(52) U.S. Cl. ..... Plt./156

(58) Field of Classification Search ..... Plt./156
See application file for complete search history.

*Primary Examiner* — June Hwu

(74) *Attorney, Agent, or Firm* — Klarquist Sparkman, LLP

(57) ABSTRACT

A new cranberry variety distinguished by very early season ripening, with exceptional early and high fruit anthocyanin (TAcy), as compared to the currently cultivated commercial varieties, with high fruit quality, and very suitable for the fresh fruit market.

2 Drawing Sheets

STATEMENT REGARDING FEDERALLY SPONSORED RESEARCH OR DEVELOPMENT

This invention was made in part with United States Government support awarded by the U.S. Department of Agriculture, Cooperative State Research, Education and Extension Service, under grant SRG 88-34155-3491.

Latin name of the genus and species of the plant claimed: *Vaccinium macrocarpon* Ait.

Variety denomination: 'CNJ95-20-20'.

BACKGROUND OF THE INVENTION

The present invention relates to a new and distinctive American cranberry variety, 'CNJ95-20-20', having a desirable combination of traits for fresh market cranberries, including intense uniformly red to dark red fruit color in early season, extremely high anthocyanin (red pigment) content, a round to ovate berry, and exceptional fresh fruit quality relative to currently cultivated commercial varieties. The variety 'CNJ95-20-20' resulted from crossing the variety 'Stevens' (unpatented) as the seed parent, with the advanced selection 'NJS98-37' (unpatented) as the pollen parent ('NJS98-37' is derived from a 'Franklin'×'Ben Lear' cross, both unpatented). 'CNJ95-20-20' was originally selected from 26 progeny of this cross, growing in a breeding trial of 3400 progeny in Chatsworth, N.J.

The American cranberry (*Vaccinium macrocarpon* Ait) is a temperate, woody perennial plant species native to North America. The United States is the largest producer, with Wisconsin and Massachusetts representing the majority of cranberry acreage and production, followed by New Jersey, Oregon and Washington. Currently cultivated cranberry varieties include selections from native populations, and first and second generation hybrids. Significant acreage remains devoted to varieties that were selected from native cranberry populations from as far back as 1850, and include the cultivars 'Ben Lear' (unpatented), 'Early Black' (unpatented), 'Howes' (unpatented), 'Lemunyon' (unpatented), 'McFarlin' (unpatented) and 'Searles' (unpatented). First generation hybrid varieties were developed from one cycle of breeding and selection that was conducted by the United States Department of Agriculture, in cooperation with state Agricultural Experiment Stations in the 1940's. This breeding program released a series of unpatented varieties in the 1950's including the most widely grown cultivar 'Stevens', which was selected from test plots in Pemberton, N.J. Recent introductions of second breeding cycle hybrids are now being planted and grown commercially.

The bulk of cranberry production is for the processed market, where varieties having high anthocyanin content, along with consistently high productivity, have become essential for commercial success. Another important cranberry market, however, is fresh fruit, where berry quality, including appearance and storage life are essential traits. A variety's crop productivity is a function of heritable traits such as stolon vigor, upright density, inflorescence bud production, fruit set and fruit size. Cultivars with high stolon vigor will establish more rapidly and reduce the number of years required to achieve maximal production. However, after bed establishment, the cultivar must transition to optimal sexual reproduction mode, and optimal upright density, to achieve high crop production. Cranberry inflorescence bud primordial, for the subsequent year's crop, are set on upright shoots during the fruit development and ripening period of the current season, and must overwinter in a dormant state, before resuming growth and flowering the following spring. Thus, the crop load of a given year, may impact the subsequent year's crop, contributing to the pronounced biennial bearing habit common to many cultivars. Productivity is also subject to environmental effects, e.g., heat and light intensity stresses, cold (frost) stress, water stress (drought and excess), disease, insects, certain pesticides, etc.

The characteristic color of cranberry arises from the synthesis of anthocyanins in the fruit epidermis during fruit ripening. Anthocyanin content is measured as TAcy (total anthocyanin), and is a fruit quality component of cranberry, having a minimum acceptable value. TAcy is measured as milligrams of anthocyanin per 100 g fruit using a standard extraction and spectrophotometric (520 nm) method. Earlier ripening varieties, which typically have higher TAcy values, and allows for an earlier season harvest of a crop. Since anthocyanins are largely located in the fruit epidermis, larger fruit generally having lower TAcy values per unit weight of fruit. The Rutgers University cranberry breeding program quantitatively measured TAcy along with mean fruit size, and selected progeny with large fruit size and high TAcy levels.

New Jersey uniquely offers an ideal environment for cranberry breeding because of the climate, soils and water. Of all the cranberry production areas in North America, New Jersey conditions subject the cranberry to the highest disease pressure and heat stress. The plant and developing fruit must tolerate high heat stress, and fruit and vegetative diseases during the growing season. Over 15 pathogens are known to incite cranberry fruit rot in New Jersey, and the fruit is also subject to heat scald and physiological breakdown. Thus, selection under New Jersey conditions offers the opportunity to identify varieties with higher resistance to disease, scald, and heat stress.

The Rutgers University cranberry breeding program, in Chatsworth, N.J., was initiated in 1985 to take advantage of this unique selection pressure. The program's methods were designed to duplicate, as practically as possible, the environment of a commercial bed. Thus, breeding plots of 1.5×1.5 m were established with multiple plants (typically one plant square ft.) and allowed to colonize area to form a dense canopy. Two to four years after planting, yield of a given plot was evaluated over a four year minimum to provide for biennial bearing assessment. Parental selection was based on field phenotypic performance, and parental cross combinations were based on the objectives of enhancing traits and/or combining the most desirable traits from both parents into one genotype, i.e., variety. Traits being evaluated in Rutgers University's cranberry breeding program include yield, ripening season, fruit rot susceptibility/resistance, storage life, scald, stolon and upright vigor, total anthocyanin content (TAcy), soluble solids (Brix), titratable acidity, and berry appearence.

The variety, 'CNJ95-20-20', described herein, resulted from a 1995 cross between the variety 'Stevens' as the seed parent, with 'NJS98-37' as the pollen parent. 'NJS98-37' is an advanced selection from a 'Franklin×Ben Lear' cross. 'CNJ95-20-20' was originally selected from 26 progeny growing in test plots in Chatsworth, N.J. for its early, uniform dark fruit color. In 2003, 'CNJ95-20-20' was planted in a replicated variety trial (3×3 m plots) in Chatsworth, N.J. for additional evaluation. 'CNJ95-20-20' was also planted in 2005 in a commercial bed (0.21 hectare) in Browns Mills, N.J. for evaluation of dry and wet harvest production. 'CNJ95-20-20' consistently produced superior quality, early-season fruit for the fresh fruit market. When dry-harvested, 'CNJ95-20-20' fruit maintains well in cold storage. 'CNJ95-20-20' is a new cranberry variety selected under New Jersey's stressful conditions, which offers the potential for high quality fruit for the fresh fruit market.

BRIEF SUMMARY OF THE INVENTION

The 'CNJ95-20-20' variety is distinguished from other cranberry varieties in having early season, uniformly dark fruit color, exceptional high fruit TAcy content, and moderate to large nearly round, ovate to widely ovate fruit shape facilitating sorting, and packaging. 'CNJ95-20-20' is most suitable for the fresh fruit market.

'CNJ95-20-20' is distinguished from the pollen parent 'NJS98-37' by the following fruit traits: 1) 'CNJ95-20-20' mean fruit weight is (2.0-2.6 g/berry), is slightly lower in weight (from 5 to 15% over years) than 'NJS98-37' (2.1-2.8 g/berry), 2) 'CNJ95-20-20' has elliptic to broadly elliptic fruit shape with a oblate stem end, whereas 'NJS98-37' fruit is elliptic to ovate with a 'pointed' stem end, 3) 'CNJ95-20-20' calyx lobes are slightly protruding and slightly appressed, whereas, 'NJS98-37' calyx lobes are distinctly protruding, 4) 'CNJ95-20-20' has waxy bloom mainly on the calyx end of the berry, whereas 'NJS98-37' has waxy bloom on over entire berry, and 5) 'CNJ95-20-20' has higher (50 to 80%) total fruit anthocyanin content (TAcy) than 'NJS98-37'.

'CNJ95-20-20' has been asexually reproduced by cuttings at the Marucci Center for Blueberry and Cranberry Research and Extension Center, NJAES, Rutgers University, Chatsworth, N.J. since 2002. Over that period, no evidence of off-types of 'CNJ95-20-20' has been observed or reported to us. Thus, it is concluded that 'CNJ95-20-20' is stable and reproduces true to type in successive generations of asexual reproduction.

The following description describes the cranberry variety 'CNJ95-20-20'. The original plant and vegetative propagules were observed in cranberry beds maintained with standard management practices for commercial cranberry production in Chatsworth and Browns Mills, Burlington County, N.J. Certain characteristics of this variety, such as growth and color, may change with changing environmental conditions (e.g., light, temperature, moisture, nutrient availability, or other factors). Color descriptions and other terminology are used in accordance with their ordinary dictionary descriptions, unless the context clearly indicates otherwise. Color designations are made with reference to The Royal Horticultural Society (R.H.S.) Colour Chart (2001).

The colors of an illustration of this type may vary with lighting and other conditions, therefore, color characteristics of this new variety should be determined with reference to the observations described herein, rather than from these illustrations alone.

DETAILED BOTANICAL DESCRIPTION

The following detailed description of the 'CNJ95-20-20' variety is based on observations of plants growing in the field in Chatsworth, N.J. and Browns Mills, N.J. The characteristics of the variety were compared to, 'Stevens' and 'Ben Lear' (both unpatented), two of the most widely cultivated cranberry varieties. The observed plantings were 3-6 years of age.

Scientific name: *Vaccinium macrocarpon* Ait.

Parentage:

*Seed parent.*—The variety 'Stevens' (derived from a 'McFarlin'×'Potters' cross).

*Pollen parent.*—The variety 'NJS98-37' (an advanced selection from a 'Franklin'×'Ben Lear' cross).

Plant:

*Vigor.*—General observations of 'CNJ95-20-20' plantings indicate average plant vigor.

*Growth habit.*—Trailing shrub with very slender stems.

*Upright length.*—8.7 cm to 9.7 cm.

*Stem diameter.*—Average stem diameter was 1.25 mm at base of current year's growth. Internodes: average internode length was 7.8 mm on 1-year old runners. Average runner length in a production bed is 68 cm (range 43-130 cm).

*Productivity.*—In established test plots in Chatsworth, N.J., 'CNJ95-20-20' yields comparably with 'Stevens' and 'Ben Lear' (Table 1). 'CNJ95-20-20' produced an average of 222 g of berries/sq. ft. (24 g/dm$^2$) in comparison to 'Steven' yield of 244 g/sq. ft. (27 g/dm$^2$), and 'Ben Lear' yield of 299 g/sq. ft. (33 g/dm$^2$) (4-year averages, see Table 1). In a 0.21 ha plot in a commercial bed, planted spring 2005, 'CNJ95-20-20' yielded 171, 256 and 261 bbl/acre for the years 2007-09, respectively.

*Petals.*—4 petals per flower; narrow and revolute in shape.

*Bloom season.*—Bloom typically begins in early June and continues throughout the month, depending on the season. Peak bloom for 'CNJ95-20-20' is similar to 'Stevens'. On Jun. 18, 2009 in Chatsworth, N.J., 'CNJ95-20-20' had reached 73% bloom while Stevens was 74% in bloom.

*Mean number of flowers per upright.*—4.0.

*Calyx.*—Diameter is 2.2 mm with non-protruding calyx lobes. Calyx lobes are less than 1 mm in length, slightly protruding and slightly appressed leaving calyx aperture somewhat exposed. Calyx lobes have waxy bloom and are slightly hirsute.

*Bud.*—Conic in shape, 7.2 mm long by 2.8 mm wide.

Fruit: Observations are from 30 typical fruit harvested from test plots in Chatsworth, N.J. and Browns Mills, N.J., Oct. 5, 2009.

Figure 1:
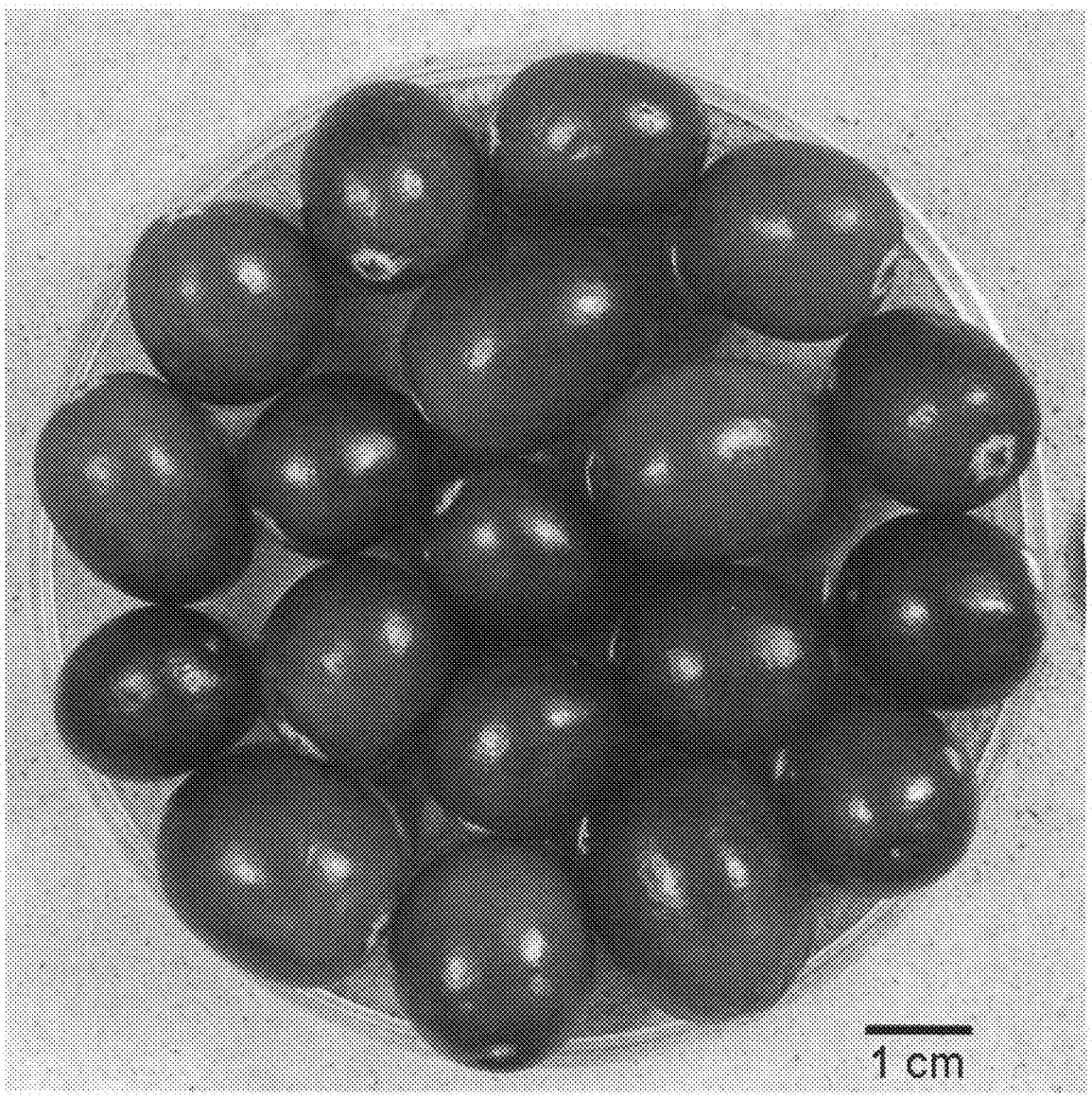
FIG. 1 is a digital image showing 'CNJ95-20-20' fruit after 5 months (Mar. 10, 2008) in cold storage from sample harvested Fall 2007 in Chatsworth, N.J.
Figure 2:
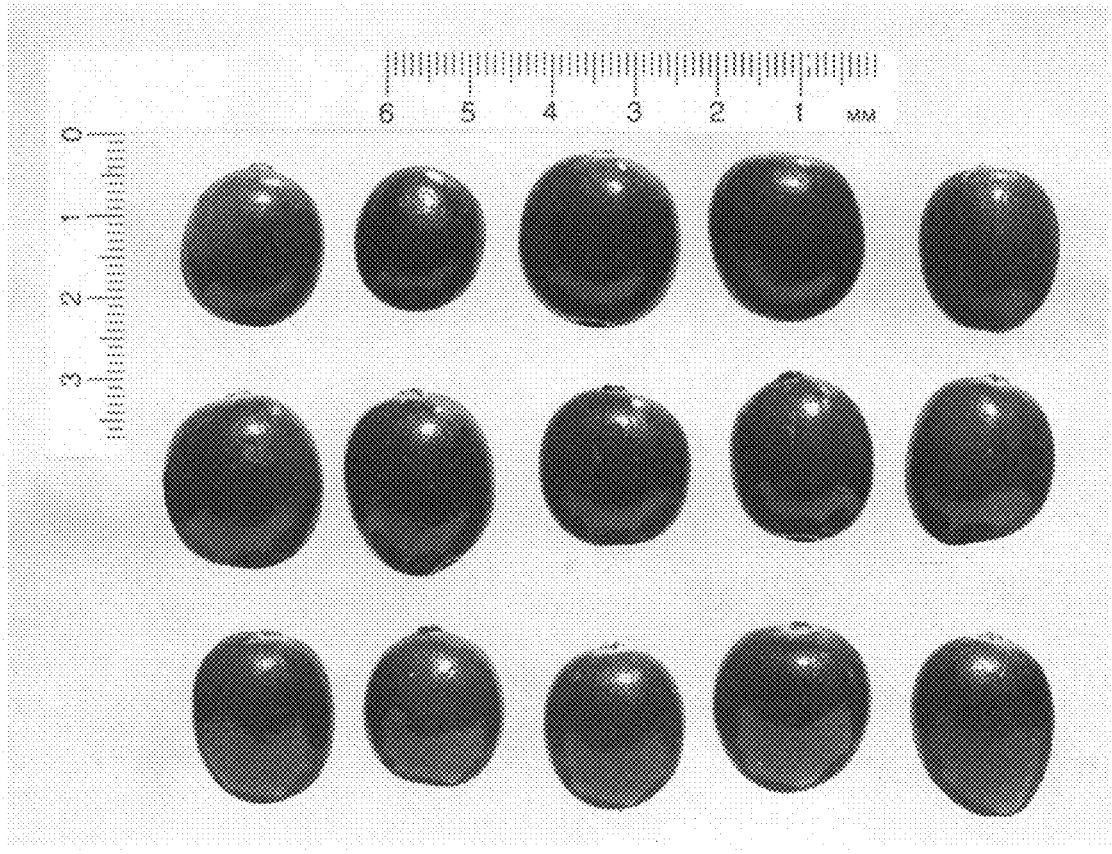
FIG. 2 is a digital image showing representative fruit of 'CNJ95-20-20' displaying the variation in fruit size, shape and color; harvested Oct. 1, 2009 in Chatsworth, N.J. Note: oblique pedicel end in fruit, particularly, second row second and last column from left.

*Shape.*—Ovate to very widely ovate to occasionally elliptical, with rounded to moderately oblique pedicle end (FIGS. 1 and 2); fruit length to width ratio of 1:1.1 to 1:1.2; calyx end slightly rounded to slightly flat with exerted calyx lobes (FIG. 2).

TABLE 1

Mean fruit yield and berry weight of 'CNJ95-20-20' relative to 'Stevens' and 'Ben Lear' during 2006-2009, in Chatsworth, NJ.

| | Yield g/sq. ft. | | | | | Mean Fruit wt., g/berry | | | | |
|---|---|---|---|---|---|---|---|---|---|---|
| Cultivar | 2006 | 2007 | 2008* | 2009 | 06-09 Mean | 2006 | 2007 | 2008* | 2009 | 06-09 Mean** |
| 'CNJ95-20-20' | 192 | 252 | 184 | 267 | 224 | 2.3 | 2.3 | 2.1 | 2.6 | 2.4 |
| 'Stevens' | 156 | 326 | 278 | 217 | 244 | 2.5 | 2.5 | 2.0 | 2.3 | 2.4 |
| 'Ben Lear' | 158 | 277 | 227 | 299 | 240 | 2.1 | 2.5 | 2.0 | 2.8 | 2.5 |

*Fruit harvested August 17 due to hail damage

**2008 data omitted

*Hardiness.*—Zones 4-7 (from USDA Misc. Publ. 814).

*Disease resistance.*—No disease resistance data available for foliar or root pathogens.

Leaves: The length, width and other measurements were obtained from observations of 30 typical fully developed leaves in November of 2008 and 2009. Color was determined on actively growing plants.

*Texture.*—Coriaceous (leathery).

*Length.*—Mean of 10.2 mm (2008-09), with a maximum 13 mm.

*Width.*—Mean of 4.3 mm and 4.9 mm for 2008 and 2009, respectively, with a maximum width of 6.0 mm.

*Shape.*—Elliptic (1.8:1 to 2.6:1 ratio).

*Apex shape.*—Rounded.

*Base shape.*—Rounded, nearly sessile.

*Margin.*—Entire, slightly revolute.

*Leaf color.*—Upper leaf surface color ranges from bright green (143C, green group) in new growth to deep green in mature leaves (139A to 137C, green group).

*Pubescence.*—Non-glandular trichomes found along leaf margins towards leaf apex.

Flowers:

*Size and shape.*—Slender, nodding flowers on erect pedicels and in clusters of typically 3-6 flowers, having a mean of 4 flowers/upright; corolla long-conic in bud, petals divided nearly to the base when open; typical open flower measuring about 10 mm across.

*Color.*—Unopened bud: deep pink (68C, red-purple group). Opened flower: pale pink (69C & D, red-purple group).

*Size.*—In NJ, average size was 1.8-2.0 cm long and 1.5-1.7 cm wide.

Figure 3:
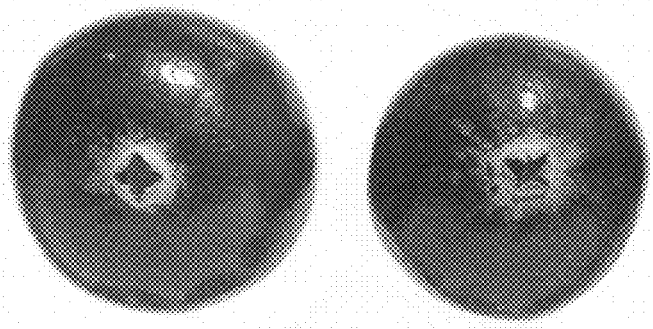
FIG. 3 is a digital image showing 'CNJ95-20-20' fruit harvested Oct. 1, 2009 exhibiting waxy bloom around calyx.

*Skin.*—Shiny, waxy bloom around calyx (FIG. 3), otherwise with slight scattered waxy bloom on lower (calyx) half.

*Color.*—Ranged from 46A (red group) for the lightest berries, 185A (greyed-purple group) for medium berries, to N186A (greyed-purple group) for the darkest (harvested fall 2007).

*Stem pit.*—Medium in width and slightly indented (1.2 mm in diameter for 'CNJ95-20-20' and 1.3 mm for Stevens).

*Average weight.*—In NJ, a 30 berry sample had a mean berry weight of 2.4 g with a maximum berry weight of 3.2 g; Fruit collected yearly from 1 ft$^2$ samples in test plots had an average weight of 2.3 to 2.6 g in NJ (Table 1).

*Number of seeds.*—Mean seed number per fruit was 19 (location 1) and 24 (location 2); a maximum of 42 seeds/fruit was observed.

*Flesh.*—N155C in color.

*Seed.*—164A to N167A in color.

*Fruit chemistry.*—100 g samples of fruit were harvested each year from test plots in Chatsworth, N.J. and evaluated for fruit chemistry. 'CNJ95-20-20' mean TAcy values were twice those of 'Ben Lear' in September, and 1.4 to 2 times greater in October (Table 2). 'CNJ95-20-20' TAcy values were three to seven times greater than 'Stevens' in September, and three to four times greater in October (Table 2). 'CNJ95-20-20' had titratable acidity values (2.2% vs. 2.5%) and Brix values (8.6% vs. 9.2%) similar to 'Stevens'.

Table 2

Fruit total anthocyanin content of 'CNJ95-20-20' relative to 'Stevens' and Ben Lear during 2006-2009, in Chatsworth, NJ.

| | Tacy, mg/100 g fruit | | | |
|---|---|---|---|---|
| | | | 2009 | |
| Cultivar | Sep. 22, 2006 | Oct. 2 2007 | Sep. 15 | Oct. 15 |
| 'CNJ95-20-20' | 59 | 56 | 62 | 75 |
| 'Stevens' | 18 | 20 | 9 | 18 |
| 'Ben Lear' | 32 | 39 | 30 | 40 |

*Fruit production.*—'CNJ95-20-20' season is very early. Fruit harvested in mid-September in New Jersey yields a Tacy of over 50 mg/100 g, exhibiting the earliest color development, much ahead of the early cultivar 'Ben Lear'. Average production was 200 to 250 g of berries/$ft^2$ in NJ test plots. The 0.21 ha plot under commercial conditions yielded up to 261 barrels/acre.

*Usage.*—Most suitable for fresh fruit market.

*Disease resistance.*—In New Jersey, where disease pressure is severe, 'CNJ95-20-20' had an average of less than 10% fruit rot (2006-2008). 'CNJ95-20-20' appears to hold very well in storage for late fresh market sales.

I claim:

1. A new and distinct variety of cranberry plant, substantially as herein shown and described.

* * * * *